United States Patent [19]

Okouchi et al.

[11] Patent Number: 4,795,630

[45] Date of Patent: Jan. 3, 1989

[54] METHOD FOR MANUFACTURING TOOTHPASTE

[75] Inventors: Haruo Okouchi; Shoji Konishi, both of Chiba, Japan

[73] Assignee: Lion Corporation, Tokyo, Japan

[21] Appl. No.: 876,169

[22] Filed: Jun. 19, 1986

[51] Int. Cl.⁴ .................................................. A61K 7/16
[52] U.S. Cl. ....................................... 424/49; 424/57; 424/58
[58] Field of Search ...................................... 424/49–58

[56] References Cited

U.S. PATENT DOCUMENTS

| | | | |
|---|---|---|---|
| 3,840,657 | 10/1974 | Norfleet | 424/49 |
| 4,292,306 | 9/1981 | Faunce | 424/52 |

FOREIGN PATENT DOCUMENTS

| | | |
|---|---|---|
| 0132844 | 11/1978 | Fed. Rep. of Germany . |
| 35-7699 | 6/1960 | Japan . |
| 52-108031 | 9/1977 | Japan . |
| 58-208208 | 12/1983 | Japan . |
| 58-208209 | 12/1983 | Japan . |

*Primary Examiner*—J. R. Brown
*Assistant Examiner*—F. T. Moezie
*Attorney, Agent, or Firm*—Birch, Stewart, Kolasch & Birch

[57] ABSTRACT

There is disclosed a method for manufacturing a toothpaste containing an abrasive, a humectant, a binder, a surfactant and water comprising steps of:

mixing the binder, part of the humectant and a small amount of water to prepare a liquid dispersion where the binder is slightly swollen, mixing the thus prepared liquid of the slightly swollen binder with the abrasive, the surfactant, the remaining humectant and the remaining water, and performing a final stage where the binder is completely swollen and dissolved to prepare a toothpaste.

13 Claims, 1 Drawing Sheet

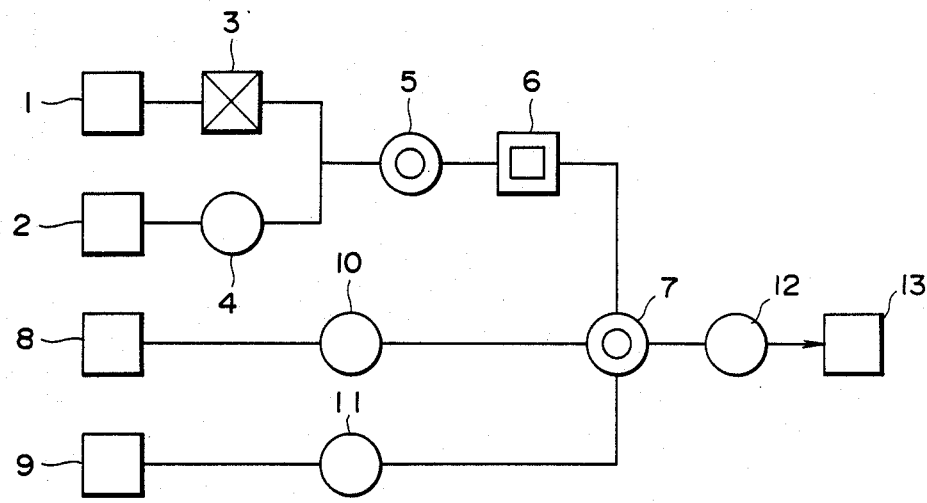

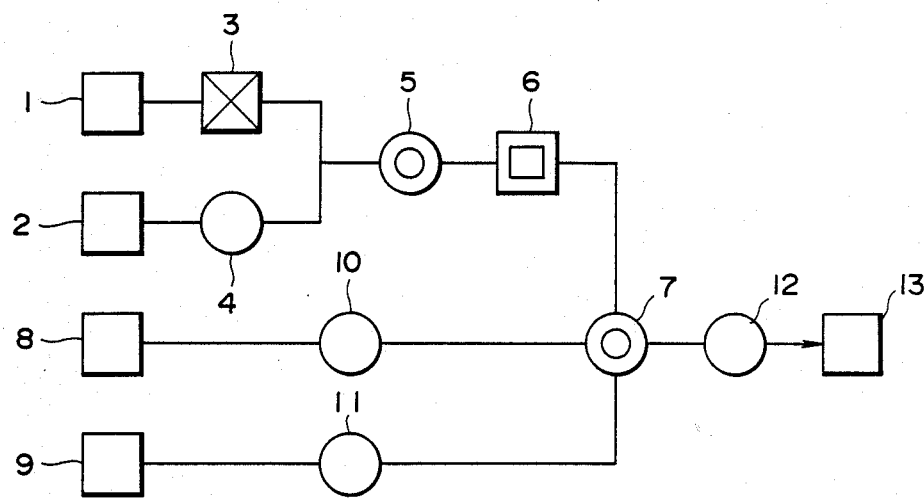

METHOD FOR MANUFACTURING TOOTHPASTE

BACKGROUND OF THE INVENTION

1. Field of the Invention

This invention relates to a method for manufacturing toothpaste which can facilitate homogeneous mixing of an abrasive, a humectant, a binder, a surfactant, water, etc. and facilitate continuous manufacture.

2. Prior Art and Its Problem

The conventional industrial method for manufacturing toothpaste comprises the steps of swelling and dissolving a binder in a mixture of a humectant and purified water, under heating if required, to prepare a solution in which the binder is completely swollen and then kneading a powdery abrasive into the thus prepared solution before the kneaded mixture is homegeneously combined with a surfactant, a flavor, an effective ingredient, etc., followed by deaerating the thus prepared mixture. In addition to this method, there are various methods for manufacturing toothpastes which are disclosed in the Japanese Patent Publication No. 35-7699 and the Japanese Patent Application Laid-open Nos. 48-40947 and 52-108,031, etc.

There is another method for manufacturing toothpaste free from air bubbles which is specified in the Japanese Patent Application Laid-open No. 58-208,208 an comprises the steps of mixing and abrasive into water or a liquid mixture composed of water and a humectant before deaeration and then adding a binder dispersed in a humectant to swell and dissolve the binder in the mixture. However, although this method is an effective batch-type manufacturing method, it is difficult to continuously and homogeneously supply a binder dispersed in a humectant because the binder easily becomes deposited and the deposited binder cannot be readily dispersed again. The incomplete dispersion of the binder may result in wide variety of the viscosity of the final product (toothpaste). Further, since the binder is rapidly swollen and dissolved in the production process to increase the viscosity of the slurry, the specific apparatus fit for high viscosity is required. Therefore this method is not suitable for continuously manufacturing toothpaste.

The method for manufacturing toothpaste free from air bubbles specified in the Japanese Patent Application Laid-open No. 58-208,209 comprises the steps of dispersing a powdery mixture containing an abrasive and a binder in a liquid mixture containing a humectant and water to prepare a slurry before deaerating it while particles of the binder exist in the slurry and then aging the deaerated slurry until the particles of the binder are completely swollen and dissolved. Although this method enables continuous manufacturing of toothpaste, the slurry must be deaerated immediately after its preparation. Additionally, there are some cases where the particle diameter and the type of the binder used, dispersion temperature and similar conditions are restricted.

SUMMARY OF THE INVENTION

Therefore, an object of this invention is to provide a method for manufacturing a toothpaste which can facilitate homogeneous mixing of the components and hence give a homogeneous toothpaste.

Another object of this invention is to provide a method for manufacturing a toothpaste continuously and efficiently.

According to this invention, there is provided a method for manufacturing a toothpaste containing an abrasive, a humectant, a binder, a surfactant and water comprising steps of:

mixing the binder, part of the humectant and a small amount of water to prepare a liquid dispersion where the binder is slightly swollen, mixing the thus prepared liquid of the slightly swollen binder with the abrasive, the surfactant, the remaining humectant and the remaining water, and performing the final stage where the binder is completely swollen and dissolved to prepare a toothpaste.

More specifically, the inventors have studied a method for continuously manufacturing toothpaste which facilitates homogeneous mixing of the components. As a result, the inventors have found that the above purposes can be effectually achieved by mixing a binder, part of a humectant and a small amount of water to prepare a liquid where the binder is slightly swollen, combining the thus obtained liquid with an abrasive, a surfactant, the remaining humectant and the remaining water, and then performing the final stage where the binder is completely swollen and dissolved. Specifically, the inventors have found that a low-viscosity liquid where a binder is slightly swollen can be prepared by mixing the binder with a humectant and a small amount of water and that an abrasive can be mixed into the thus prepared liquid to prepare a slurry from which air bubbles can be easily removed and which can be easily homogenized by agitation. They have also found that the components of the thus obtained toothpaste are homogeneously blended. because the slightly swollen binder is easily and completely swollen and dissolved in the final process performed after mixing the components. The present invention is completed by the above findings.

BRIEF DESCRIPTION OF THE ACCOMPANYING DRAWING

The above and other objects, features and advantages of the present invention will be more clearly understood by the following description with reference to the accompanying drawing which represents a flow chart explaining one embodiment of the method according to this invention.

DETAILED DESCRIPTION OF THE INVENTION

The method for manufacturing a toothpaste containing an abrasive, a humectant, a binder, a surfactant and water according to this invention comprises the steps of mixing the binder with a part of the humectant and a small amount of water to prepare a liquid where the binder is slightly swollen, mixing the thus obtained liquid with the abrasive, the surfactant, the remaining humectant and the remaining water, and then performing the final stage where the binder is completely swollen and dissolved.

In this invention, secondary calcium phosphate dihydrate and anhydrate, tertiary calcium phosphate, calcium carbonate, aluminum hydroxide, alumina, insoluble sodium metaphosphate, calcium pyrophosphate, crystalline silica, noncrystalline silica, magnesium carbonate, magnesium phosphate, a synthetic resin powder, etc. can be used as the abrasive. Any of these compounds can be used alone or a combination of them can be used. Although there is no restriction on the amount of abrasive used, it usually constitutes 5 to 60% by weight of the resulting toothpaste.

Polyvalent alcohols such as glycerol, propylene glycol, sorbitol, polyethylene glycol, polypropylene glycol, xylitol, maltitol, lactitol, etc. can be used as the humectant. These compounds can be used either singly or in combination. Although the amount of the humectant used varies according to the type of toothpaste, it usually constitutes 5 to 70% by weight of the toothpaste.

Any binders which are swollen and dissolved in water can be used. Examples of the binder include cellulose derivatives such as sodium carboxymethylcellulose, methylcellulose and hydroxyethyl cellulose, carrageenan, alkali metal alginates such as sodium alginate, gums such as xanthane gum, tragacanth gum, karaya gum and gum arabic and synthetic binders such as polyvinyl alcohl, sodium polyacrylate and carboxyvinyl polymer. Any of these compounds can be used alone or a combination of them can be used. Although there is no restriction on the amount of the binder used, it usually constitutes 0.3 to 5% by weight of the toothpaste.

As the surfactant, anionic surfactants suoh as sodium lauryl sulfate, sodium myristyl sulfate, sodium palmityl sulfate, a higher fatty acid soap, sodium $\alpha$-olefin sulfonate and an N-acylated amino acid, nonionic surfactants such as lauroyl diethanolamide, sucrose fatty acid esters and polyoxyethylene sorbitan monolaurate and ampho- teric surfactants can be used. Any of these compounds or a combination of them constitutes 0.1 to 7% by weight of the toothpaste.

The method of this invention is performed by first mixing the binder, part of the humectant and a small amount of water to prepare a liquid where the binder is slightly swollen.

In order to prepare a liquid dispersion composed of the binder homogeneously dispersed in the humectant which has almost constant viscosity and flowability and in which no precipitate of the binder occurs, it is preferable that the binder is homogeneously dispersed in the humectant before a small amount of water is added to the thus prepared liquid dispersion. In this process, propylene glycol, polyethylene glycol and polypropylene glycol are preferable as the binder used herein because of their property on dispersing the binder efficiently and homogeneously.

In order to prepare a liquid containing a slightly swollen binder which has low viscosity and readily flows through pipes and in which the binder is favorably swollen and no precipitation of the binder occurs and to easily and completely effect the swelling and dispersion of the binder in the final stage of the procedure, it is preferable that the amount of water in the above liquid may be 5 to 40% by weight, preferably 8 to 20% by weight of the amount of the binder. Moreover, it is preferable that the amount of binder may be 20 to 50% by weight of humectant. It is also preferable that the viscosity of the above liquid at room temperature may be less than 5 poises.

In the next process step of the method of this invention, the abrasive, the surfactant and the remaining huemectant are added to the liquid containing a slightly swollen binder. The remaining water is added either during or after these ingredients are mixed with the liquid containing a slightly swollen binder in order to achieve complete swelling and dispersion of the binder in the final process step. Accordingly, it is possible to mix the abrasive and the other ingredients into the liquid while the binder is maintained in a slightly swollen state, thereby enabling the resulting slurry to be easily homogenized.

In the invention, in addition to the above. ingredients, a sweetener, a flavor, a preservative, an effective ingredient, etc. may be blended as required.

As the sweetner, saccharin sodium, sucrose, maltose, lactose, stevioside, neohesperidildigydrochalcone, glycyrrhizin, perillartine, p-methoxycinnamic aldehyde and the like may be used in an amount of 0.05 to 5% by weight of the toothpaste. Essential oils such as spearmint oil, peppermint oil, salvia oil, eucalyptus oil, lemon oil, lime oil, wintergreen oil and cinnamon oil, other spices and fruit flavors as well as isolated and synthetic flavoring materials such as l-menthol, carvone, anethole, eugenol and the like can be used as flavors. The flavor may be blended in an amount of 0.1 to 5% by weight of the toothpaste. Ethyl paraoxy benzonate, butyl paraoxy benzoate, etc. may be used as the preservative. The sweetner may be added with the abrasive. The flavor and the preservative may be added when preparing the liquid of the slightly swollen binder or mixed with binder after mixing with the humectant. Enzymes such as dextranase, lytic enzyme, lysozyme, amylase and antiplasmin agents such as $\epsilon$-aminocaproic acid and tranexamic acid, fluorine compounds such as sodium monofluorophosphate sodium fluoride and stannous fluoride, chlorhexidine salts, quaternary ammonium salts, aluminum chlorohydroxyl allantoin, glycyrrhetinic acid, chlorophyll, sodium chloride and phosphoric compounds may be used as the effective ingredient. Moreover, silica gel, aluminum silica gel, organic acids and their salts may be blended as desired. An organic effective ingredient with low viscosity may be added when preparing the liquid of the slightly swollen binder.

When performing the method of this invention for manufacturing toothpaste, there is no special restriction on the procedure for combining the liquid containing the slightly swollen binder with the abrasive, the remaining humectant, the surfactant, the remaining water and the other ingredients. For example, when the surfactant is powder, the abrasive and the surfactant are mixed using a mixer such as a ribbon mixer to prepare a powdery mixture and the other water-soluble ingredients are dissolved in a liquid mixture composed of the remaining humectant and the remaining water. Next, the thus prepared powdery mixture and liquid dispersion are mixed together, followed by deaerating the mixture to prepare a slurry free from bubbles. After that, the thus prepared slurry and the liquid of the slightly swollen binder are mixed together to make a dispersion, When the surfactant is liquid, it is dispersed in a liquid mixture of the remaining humectant and the remaining water. Even when the surfactant is powdery, it can be dispersed in part of the water before the thus prepared liquid is mixed with the remaining humectant and the remaining water. Furthermore, it is also possible to mix an aqueous solution of the surfactant to be described later with the remaining humectant and the remaining water.

Deaeration, which is necessary in any of the above methods, can be performed either on the slurry of the abrasive or while mixing the abrasive, the liquid of the slightly swollen binder, the remaining humectant, the remaining water and the surfactant together.

However, the most favorable effect can be achieved by the following method of deaeration. After the binder is dispersed either in part of the humectant or in a solution prepared by mixing part of the humectant with a low-viscosity organic effective ingredient, a flavor and other water insoluble ingredients as required, a small amount of water is added to the thus prepared dispersion to obtain a liquid where the binder is slightly swollen. The abrasive is mixed with part of the water, the remaining humectant or a mixture composed of the remaining humectant and part of the water, followed by deaerating the thus prepared mixture to obtain a slurry of the abrasive. Thereafter, the remaining part of the water is mixed with the surfactant and then the thus prepared mixture is combined with other water-soluble ingredients before deaerating the mixture to obtain an aqueous solution of the surfactant. After that, the thus obtained liquid of the slightly swollen binder, the slurry of the abrasive and the aqueous solution of the surfactant are mixed and dispersed together, thereby efficiently preparing toothpaste free from air bubbles. Otherwise, during deaeration of the slurry, the existence of the surfactant may produce unfavorable effect in many cases. And, some water-soluble ingredients and organic effective ingredients may adversely effect dispersion of the abrasive.

This method will be described in the following with reference to the drawing. In the figure, the numeral (1) represents an abrasive and the numeral (2) represents water and/or the humectant. After given amounts of the abrasive (1) and water and/or the humectant (2) are mixed by continuously feeding them into the mechanism (5) for continuously dispersing the solid into the liquid by means of the quantitative feeder (3) for supplying a given amount of powder and the quantitative pump (4) for supplying a given amount of water and/or the humectant, the slurry is deaerated with the mechanism (6) for continuously deaerating the slurry under reduced pressure, and then the deaerated slurry is introduced into the device (7) for continuously dispersing the solid into the liquid. The numeral (8) represents a liquid where the binder is slightly swollen which is prepared by mixing the binder with the humectant, a small amount of water, the water-insoluble effective ingredient and the flavor. The numeral (9) represents a solution of the surfactant which is prepared by dissolving the surfactant, the sweetener and the water-soluble effective ingredient into water before deaerating the thus prepared solution by leaving it without any agitation. Given amounts of the liquid (8) and the surfactant solution (9) are continuously introduced by pumps (10) and (11) into the device (7). After the abrasive slurry, the liquid dispersion (8) and the surfactant solution (9) are mixed together in the device (7) to prepare a toothpaste slurry, this slurry is fed by a pump (12) to a product tank (13) to obtain toothpaste in which the binder is completely swollen and dissolved.

By this method for deaerating the slurry with low concentration prepared by mixing the abrasive with water and/or the humectant the air bubbles can be easily removed favorably and therefore a stable toothpaste with high quality can be efficiently and continuously prepared.

As described above, the ingredients can be mixed while maintaining low viscosity by the method for manufacturing toothpaste according to this invention. Therefore, homogeneous dispersion of all of the ingredients including the binder can be easily achieved. Besides, as the binder is slightly swollen by a slight amount of water and then the solution of the slightly swollen binder is combined with a great amount of water in the final stage, the binder can be easily swollen and dissolved completely during passing through the pump and the transfer pipe. The liquid of the slightly swollen binder can be easily transferred through a pipe due to its low viscosity. More specifically, since the slurry in which the binder is swollen and dissolved is highly viscous but thixotropic, the discharge power required for transferring the slurry can be considerably small as compared with that for a standing slurry having the same viscosity. It can also be supplied to the mixer by means of a simple device because no precipitation of the binder occurs in the liquid. Moreover, the amount of the binder contained in the resulting slurry can be adjusted accurately. Accordingly, the method of this invention enables toothpaste, to be efficiently manufactured continuously and also enables air bubbles to be removed while maintaining low viscosity of the slurry.

This invention will be described in more detail according to examples in the following by way of illustration and not by way of limitation.

EXAMPLE 1

| | | |
|---|---|---|
| Secondary calcium phosphate | 40.0% | by weight |
| Sorbitol (70% aqueous solution) | 30.0 | |
| Polyethylene glycol | 5.5 | |
| Sodium lauryl sulfate | 1.0 | |
| Coconut oil fatty acid diethanolamide | 0.5 | |
| Carrageenan | 1.0 | |
| Sodium saccharinate | 0.2 | |
| Flavor | 1.0 | |
| Ethyl paraoxy benzoate | 0.01 | |
| Purified water | Remaining part | |
| Total | 100.0% | by weight |

Polyethylene glycol was combined with a flavor, coconut oil fatty acid diethanolamide and ethyl paraoxybenzoate and then carrageenan was mixed into the thus prepared mixture while agitating it. After that, 0.1% by weight of the toothpaste of purified water (10% by weight of the carrageenan) was added to prepare a liquid where carrageenan used as the binder was slightly swollen. Separately, after sodium lauryl sulfate and sodium saccharinate were added to 5% by weight of the toothpaste of purified water before agitating the mixture to prepare a solution, this solution was deaerated by leaving it without agitation thereby preparing an aqueous surfactant solution.

A mixture composed of secondary calcium phosphate, 70% aqueous sorbitol solution and the remaining purified water in a given ratio was continuously supplied into a device for continuously dispersing the solid into the liquid (flow jet mixer, manffactured by Konaken Co., Ltd.). About 430 kg of the above mixture was treated in this device the interior of which was evacuated to a 30 to 60 mmHg vacuum and maintained at this vacuum. Thus, an abrasive slurry containing no air bubbles was prepared.

Next, the above liquid where the binder was slightly swollen, aqueous surfactant solution and abrasive slurry were continuously supplied in a given ratio into a device for continuously dispersing the solid into the liquid (flash mixer manufactured by Takara Koki Co., Ltd.) by means of quantitative pumps. In this process, 500 kg/hr of the mixture was treated by this device and the obtained slurry was fed by a product pump to the product tank to prepare a smooth stable toothpaste free from air bubbles.

EXAMPLE 2

| Noncrystalline silica | 15.0% | by weight |
| --- | --- | --- |
| Sodium α-olefin sulfonate | 1.0 | |
| Sodium carboxymethylcellulose | 1.0 | |
| Propylene glycol | 5.5 | |
| Sorbitol (60% aqueous solution) | 45.5 | |
| Glycerol | 20.0 | |
| Sodium saccharinate | 0.2 | |
| Flavor | 0.8 | |
| Buthyl paraoxybenzonate | 0.01 | |
| Purified water | Remaining part | |
| Total | 100.0% | by weight |

A flavor and methyl paraoxybenzoate were added to 5% by weight of the toothpaste of propylene glycol and then sodium carboxymethylcellulose was mixed into the thus prepared mixture while agitating it. After that, 0.2% by weight of the toothpaste of 60% aqueous sorbitol solution (the amount of water was 12% by weight of the amount of sodium carboxylmehylcellulose) was added to prepare a liquid where sodium carboxymethylcellulose used as the binder was slightly swollen. Separately, after sodium α-olefin sulfonate, sodium saccharinate and the remaining propylene glycol (0.5% by weight were added to 7% by weight of the toothpaste before agitating the mixture to prepare a solution, this solution was deaerated by leaving it without agitation thereby preparing an aqueous surfactant solution.

After noncrystalline silica, glycerol, the remaining 60% aqueous sorbitol solution and the remaining purified water were mixed by a device for continuously dispersing the solid into the liquid (flow jet mixer) to prepare a dispersion, the dispersion was passed through a device for continuously deaerating a mixture (Basadar, manufactured by Colonel company) to prepare an abrasive slurry containing no air bubbles.

Next, the above liquid where the binder was slightly swollen, aqueous surfactant solution and abrasive slurry were supplied in a given ratio into a device for continuously dispersing the solid into the liquid (line homomixer manufactured by Tokushu Kika Industry Co., Ltd.) by means of quantitative pumps. In this process, 1,000 kg/hr of the mixture was treated by this device and the obtained slurry was fed by a product pump to the product tank to prepare a smooth stable transparent toothpaste free from air bubbles.

What is claimed is:

1. A method for manufacturing a toothpaste containing an abrasive, a humectant, a binder, a surfactant and water comprising the steps of:
   (a) mixing said binder, a glycol selected from the group consisting of propylene glycol, polyethylene glycol and polypropylene glycol as a component of said humectant, and a portion of said water in an amount of 5 to 40% by weight of the binder to prepare a liquid dispersion where the binder is slightly swollen,
   (b) mixing the thus prepared liquid containing the slightly swollen binder with an abrasive, said surfactant, the remaining humectant and the remaining portion of said water, and
   (c) performing a final stage wherein the binder is completely swollen and dissolved to prepare a toothpaste.
2. The method as set forth in claim 1 wherein the liquid where the binder is slightly swollen, an abrasive slurry prepared by mixing the abrasive into part of the water, the remaining humectant or a liquid mixture composed of part of the water and the remaining humectant and an aqueous surfactant solution prepared by dissolving the surfactant into the remaining water are mixed together to make a dispersion which is left to completely swell and dissolve the binder, whereby the toothpaste is prepared.
3. The method as set forth in claim 2 wherein the abrasive slurry and the aqueous surfactant solution are deaerated before they are mixed with the liquid of the slightly swollen binder to make the dispersion, whereby a toothpaste free from bubbles is prepared.
4. The method as set forth in claim 1, wherein at least one abrasive is selected from the group consisting of secondary calcium phosphate dihydrate and anhydrate, tertiary calcium phosphate, calcium carbonate, aluminum hydroxide, alumina, insoluble sodium metaphosphate, calcium pyrophosphate, crystalline silica, noncrystalline silica, magnesium carbonate, magnesium phosphate, and a synthetic resin powder.
5. The method as set forth in claim 1, wherein said humectant is a mixture of:
   a glycol humectant selected from the group consisting of propylene glycol, polyethylene glycol and polypropylene glycol, and
   at least one humectant selected for the group consisting of glycerol, sorbitol, xylitol, maltitol, and lactitol.
6. The method is set forth in claim 1, wherein said binder is selected from at least one of the group consisting of sodium carboxymethylcellulose, methylcellulose, hydroxyethyl cellulose, sodium alginate, xanthane gum, tragacanth gum, karaya gum, gum arabic, polyvinyl alcohol, sodium polyacrylate and carboxyvinyl polymer.
7. The method as set forth in claim 1, wherein said surfactant is selected from at least one of the group consisting of an anionic surfactant, a nonionic surfactant and an amphoteric surfactant.
8. The method as set forth in claim 1, wherein in step (a) the binder is present in an amount of 20 to 50% by weight of the humectant.
9. The method as set forth in claim 1, wherein the viscosity of the liquid dispersion in step (a) at room temperature is less than 5 poises.
10. The method as set forth in claim 1, further comprising mixing in step (b) at least one of the following ingredients a sweetener, a flavor, a preservative, an oil, an enzyme, and a fluorine containing compound.
11. The method as set forth in claim 1, wherein in step (a) the water is 8 to 20% by weight of the amount or binder.
12. A continuous method for manufacturing a toothpaste containing an abrasive, a humectant, a binder, a surfactant and water comprising the steps of:
   (a) mixing said binder, a glycol selected from the group consisting of propylene glycol, polyethylene glycol and polypropylene glycol as a component of said humectant, and a portion of said water in an amount of 5 to 40% by weight of the binder to prepare a liquid dispersion where the binder is slightly swollen; and
   (b) mixing the this prepared liquid containing the slightly swollen binder with an abrasive slurry, an aqueous surfactant solution, the remaining humectant and the remaining portion of said water to achieve complete swelling and dispersion of the binder.

13. The method as set forth in claim 12, wherein the abrasive slurry and the aqueous surfactant solution are deaerated before they are mixed with the liquid of the slightly swollen binder to make the dispersion, whereby a toothpaste free from bubbles is prepared.

* * * * *